United States Patent [19]
Smith

[11] Patent Number: 5,133,708
[45] Date of Patent: Jul. 28, 1992

[54] METHOD FOR CONTROLLED CORNEAL ABLATION

[76] Inventor: Robert F. Smith, 100 Cerasi Dr. Apt. 208, West Mifflin, Pa. 15122

[21] Appl. No.: 368,667

[22] Filed: Jun. 19, 1989

Related U.S. Application Data

[63] Continuation-in-part of Ser. No. 143,835, Jan. 14, 1988, abandoned.

[51] Int. Cl.⁵ .............................................. A61N 5/06
[52] U.S. Cl. ...................................... 606/5; 606/16; 606/17; 128/395; 128/397; 128/398; 128/898
[58] Field of Search ................ 128/395, 397, 398, 898; 606/5, 13–18

[56] References Cited

U.S. PATENT DOCUMENTS

| 3,945,375 | 3/1976 | Banko | 128/6 |
| 4,461,294 | 7/1984 | Baron | 128/395 |
| 4,729,372 | 3/1988 | L'Esperance, Jr. | |

FOREIGN PATENT DOCUMENTS

| 222537 | 5/1987 | European Pat. Off. | 606/5 |

*Primary Examiner*—David Shay

[57] ABSTRACT

A method for effecting controlled refractive correction of the cornea comprising a contact lens whose concave surface is wetted with an inert ultraviolet absorbent liquid. An excimer laser feeds a cylindrical bundle of quartz fibers terminating angularly in a decollimating matrix at the contact lens in such manner as to attenuate the ultraviolet flux in said liquid proportional to the depth thereof at the cornea so as to effect greatest corneal ablation at the thinnest depth of the liquid.

6 Claims, 2 Drawing Sheets

METHOD FOR CONTROLLED CORNEAL ABLATION

This application is a continuation-in-part of U.S. patent application Ser. No. 143,835, filed Jan. 14, 1988 now abandoned.

This invention relates to a method and apparatus for controlled corneal ablation of the human cornea to achieve refractive correction of either myopia, hyperopia, regular or irregular astigmatism, and to minimize the effects of presbyopia. More particularly, the present invention utilizes electromagnetic radiation such as an ultraviolet laser at a wavelength of 193 nm whose radiation is intercepted and subdivided by a bundle of optical fibers having their radiation emitting ends arranged to simultaneously expose the optically used corneal surface to radiation modulated by a contact lens constraining an inert UV absorbing liquid to produce the desired optical reshaping and at the same time minimizing exposure of other eye tissues to the radiation.

BACKGROUND OF THE INVENTION

Recent investigations have demonstrated that UV far (ultraviolet) radiation produced by an excimer laser at a wavelength of 193 nm can ablate (remove) corneal tissue with minimal trauma, loss of transparency or scarring. The ablative process that occurs using this far UV wavelength region primarily results from the breakup of intramolecular bonds as reported by Trokel, et. al., in the *American Journal of Ophthalmology*, Volume 96, No. 6, December, 1983, Entitled: "EXCIMER LASER SURGERY OF THE CORNEA". This action is in contrast with that produced by higher wavelength laser radiation in the infrared region where tissue destruction results from thermal heating and the precision of tissue removal is much degraded.

The lens of the eye will absorb all 193 nm UV radiation by the application of Beer's law of light transmission given by $T = 10^{-ad}$, where T is the transmission (100% = 1.0), a is the absorbance and d is the thickness of the material. For bovine lenses $a = 1360/cm$ at 193 nm, a value close to that of human eye lenses. Thus 90% absorbance product of a and d equal to 1.0 i.e., $d = 1/1360 = 7.35$ um (microns). For thicknesses 10 times this value, the transmission through the lens would be 1 part in 10 billion. Thus, it appears that the lens will totally protect the retina of the eye from 193 nm UV. However, very low levels of 193 nm UV, such as might be able to penetrate the cornea and aqueous humor could possibly damage the lens in a manner similar to longer wavelength UV radiation causing cataracts. Therefore, precaution to avoid exposing the lens to any amount of 193 nm UV is either necessary or desirable.

Some experimentation with in-vivo eyes using total corneal surface ablation with 193 nm UV has shown a tendency towards some hazing/cloudiness of vision. The clouding effect suggests that the angle of impingement of UV may be critical.

There presently exist a number of techniques to modify corneal shape using lasers for purposes of refractive correction. These include radial keratotomy, lamellar keratectomy correction (keratomileusis), and direct corneal shaping via ablation. Baron, is U.S. Pat. No. 4,461,294, implements the first of these (radial keratotomy) by imbedding laser light absorbing particles in a radial pattern, then vaporizing these particles by laser radiation to produce the radial scar tissue characteristic of the technique. Trokel, et. al., discussed above, and European Patent No. 0 151 869 discuss full surface corneal ablation using the excimer laser. In the Trokel paper and the European patent, no means for protecting of critical eye tissue is given. Belgorod, in U.S. Pat. No. 4,724,522, describes an apparatus and method allowing full protection of eye tissue.

The present invention is uniquely distinguished from the present known prior art in regard to both apparatus and method: In Baron, the method is limited to performing radial keratotomy which mandates the formation of scar tissue (eschewed in the present invention); also, the opaque contact lens therein plays no role in corneal shaping, serving only to shield the eye from laser radiation; and the reference to fiber optics is solely for delivering radiation along the radial slits. In Belgorod's apparatus, the system of mechanical rotational and linearly transrotational mirror elements is inherently complex—requiring high precision in construction and application to achieve the desired ablative sculpting by the excimer laser. This contrasts with the present invention, which rather than sculpting the cornea one area at a time, operates simultaneously over the total cornea, doing so with minimal precision requirements.

SUMMARY OF THE INVENTION

The object of the present invention is to provide a system for corneal reshaping to achieve refractive correction of refractive errors of the human eye.

According to the present invention, there is provided a method and apparatus wherein an electromagnetic wave generator, preferably a far UV laser (wavelengths less than 200 nm) whose collimated output beam of radiation is captured by one end of the bundle of small diameter far UV transparent optical fibers, the other end of said bundle placed in close proximity with the cornea where individual fibers are selectively angled by means of a decollimating matrix to conduct the UV radiation to the cornea while at the same time minimizing exposure to far UV radiation of all other tissues. Selective attenuation of UV radiation intensity to ablate a desired corneal surface is accomplished by passing the decollimated radiation through a UV transparent lens, which lens constrains an inert UV absorbing liquid between it and the cornea.

A device for full surface ablation of the in vivo/in situ or in vitro cornea consisting of an arrangement of ultra violet transmitting fibers, limited in number and size only by the principles of multi-mode or single mode fiber optic physics and limited in length only by the UV absorption properties of the material used. The optical fibers intercepting a beam of UV radiation of desired cross sectional area at one end and at the other end, in proximity with the cornea, each fiber being directed by means of a decollimating matrix interface wherein the angle of incidence upon the cornea of UV radiation from each fiber, the angle of cleavage of each fiber, the geometrical pattern arrangements of fibers and the variation of refractive indices and UV arrangements of fibers and the variation of refractive indices and UV absorptive properties of fibers, intervening intensity modulating filters and liquids is unrestricted.

DETAILED DESCRIPTION OF THE INVENTION

Figure 2:
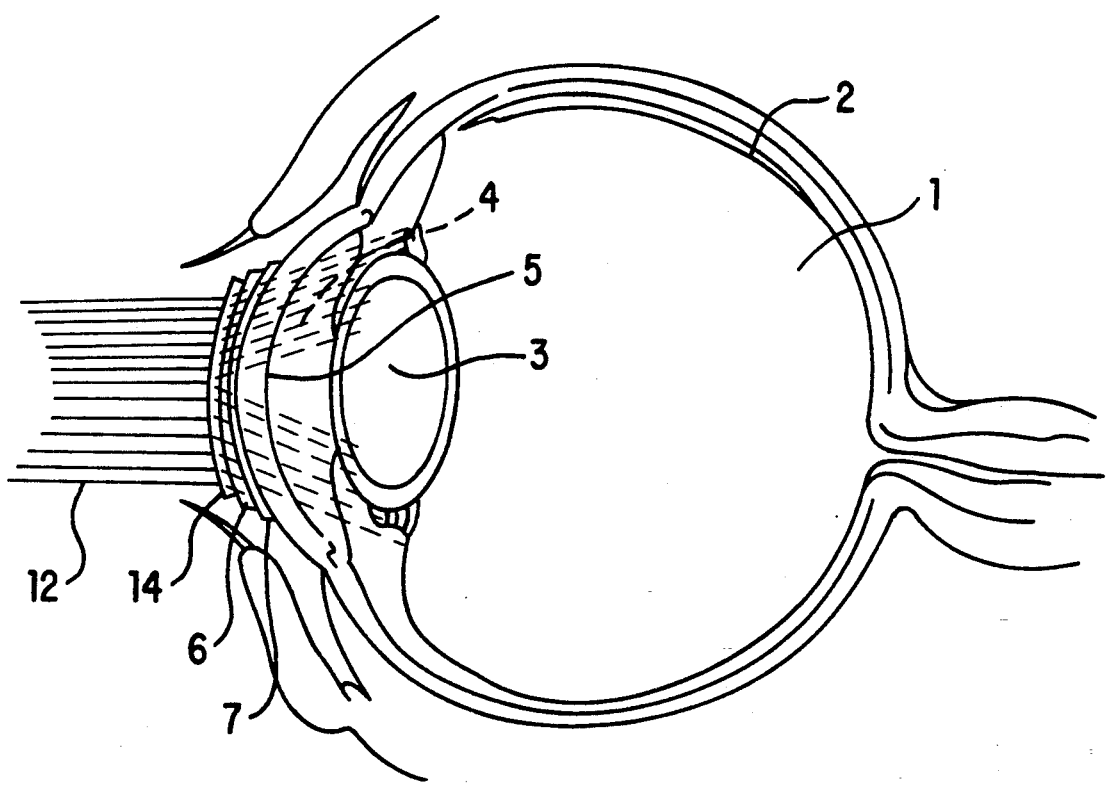
FIG. 2 is an enlarged partial view of FIG. 1.

Referring to FIG. 2 which shows a human eye, numeral 1 denotes the vitreous humor at the rear of which appears the retina 2 and forwardly the lens 3, iris 4 and cornea 5.

Figure 1:
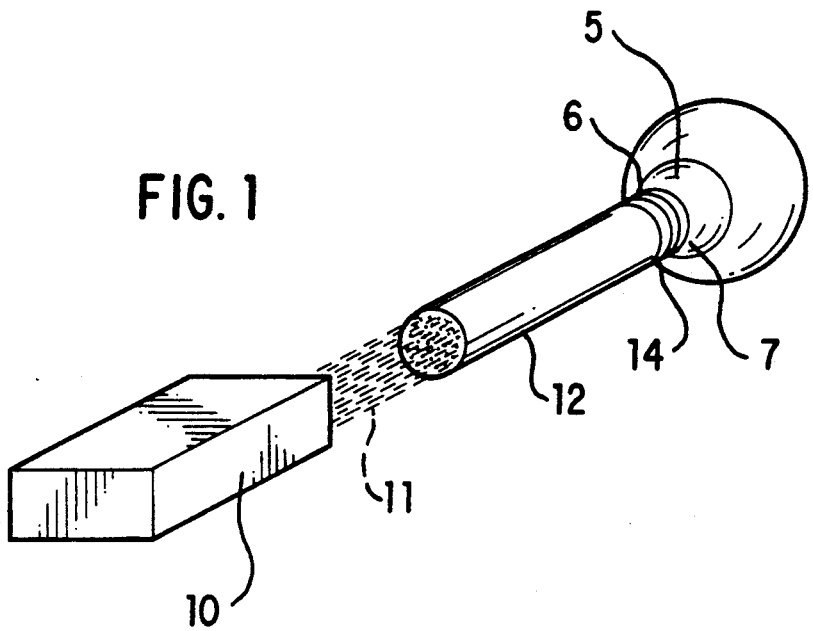
FIG. 1 is a perspective view which shows the excimer laser fiber optic matrix system for ablating the cornea of the eye to achieve refractive correction according to the present invention.

FIG. 1 shows the components of the system and their interrelation to one another. Beginning with the excimer laser 10, its collimated beam 11 is aligned with a cylindrical bundle 12 of quartz fibers, each on the order of 20-100 um diameter. The fibers then terminate in a decollimating matrix 14 consisting of a flexible plastic disk. Here, the term matrix is used to emphasize the fact that each fiber element is inserted into the flexible plastic at a specified angle of incidence. Then, this matrix is placed over a custom ground quartz contact lens 6 (of zero power)—the curvature of the inside surface being the predetermined optimum corneal curvature determined for the particular patient. Lastly, a liquid 7 is placed between the contact lens and corneal surface 5 and sufficient pressure is applied to prevent any air voids. The characteristics of the liquid are (1) chemical inertness, and (2) an ultraviolet absorbance factor proportional to depth.

The basic principle of operation is as follows: Each fiber receives an equal amount of ultraviolet flux which is then transmitted to the matrix. The incident flux from each fiber is injected at a prescribed angle by the matrix into the contact lens/inert liquid 7 interface where it is attenuated proportional to the depth of the liquid.

FIG. 2 given an illustration of how corneal ablation can be controlled to correct for myopia. As shown, the contact lens 6 surface is shallower than the surface of the cornea. Then, because the ultraviolet absorbing liquid 7 is shallower at the center of the cornea than the periphery, the greatest rate of ablation occurs at the center, gradually diminishing towards the periphery. The overall effect is that the shape of the cornea is ablated to approach that of the inner surface of the contact lens.

The cross sectional illustration in FIG. 2 also shows one possible scheme for orientation of the fibers. Here, the angling is chosen to minimize refracting remanent light flux (shown by the dotted lines) to the central axis of the eye while still maintaining the desired uniformity of flux on the cornea itself.

Ideally, the liquid 7 should be inert, to avoid any chemical reaction with corneal tissue, should attenuate (but not block) UV radiation, and should have high (inter/intra) molecular bonding so as to minimize ablation/vaporization of the liquid 7 itself. Glycerin (glycerol) is an example of a liquid approaching these desired properties because it begins to attenuate UV radiation below 220 nm, is relatively inert and nox-toxic. Further, glycerin's high boiling point (290° C.) and high energy of formation (−668 kJ/mol) indicate a considerably higher molecular bonding than is associated with corneal tissue. Consequently, what radiation is absorbed by the glycerin liquid will be converted into heat thereby raising its temperature, but the glycerin liquid will experience little ablation/vaporization. Because it is anticipated that the cornea will be ablated for a number of periods each lasting only several seconds, the problem of heat buildup in the liquid (e.g. glycerin) can be limited. Also, after each treatment period, the fiber optic bundle, decollimating matrix, and/or contact lens would be removed, liquid (glycerin) be flushed from the cornea along with ablation products contained therein. For longer periods of treatment time it may be desirable to provide for a continuous laminar flow of the liquid between contact lens 6 and cornea 5 by means of capillary tubes providing for a continual removal of ablation products while avoiding heat buildup in the liquid 7.

The advantages and novelty of the system are:

1. Simultaneous ablative processing of the full corneal surface, obviating such problems as laser output variations versus time, criticality of corneal positioning, and excessive time requirements otherwise required in corneal shaping.

2. Inherent iterative convergence of the technique—the corneal shaping always proceed in the direction of matching the corneal surface with that of the contact lens. This characteristic enables a degree of optical precision and predictability unattainable with other methods of corneal refraction adjustment.

3. Safety both in regard to the minimization of ultraviolet flux into the eye and the fact that the technique is entirely non-invasive.

Figure 3:
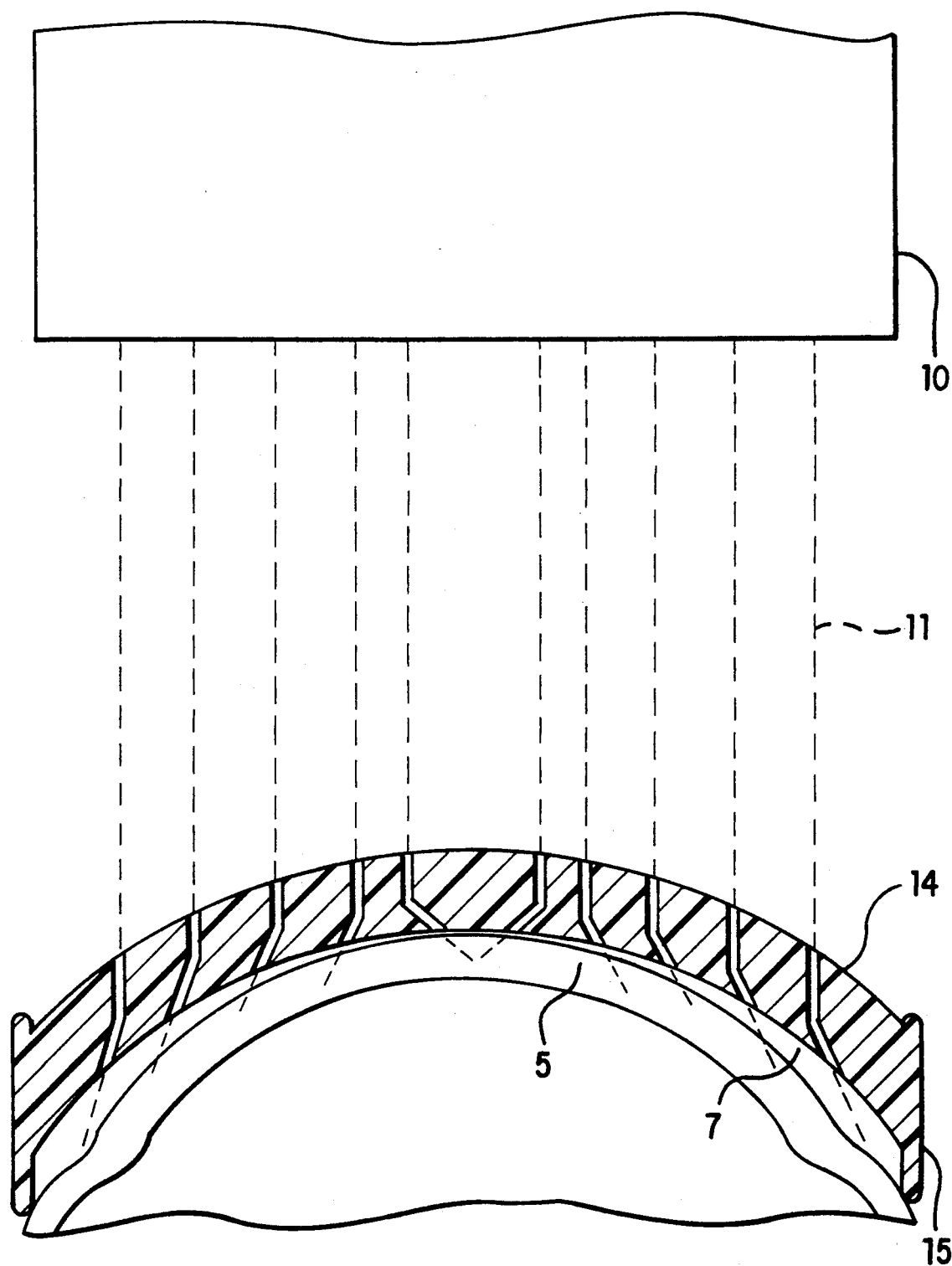
FIG. 3 is an enlarged view in section illustrating a decollimating matrix.

4. FIG. 3 shows a modification similar to the system shown in FIGS. 1 and 2 except for the insertion, in the system, of an ultraviolet filter 13 of desired non-uniform transparency to ultraviolet across its surface.

FIG. 3 shows an embodiment of the invention offering minimal complexity both in regard to design and application. Beginning with the exciter laser 10, its collimated output beam is aligned with a cylindrical bundle of fibers 12, all parallel with one another and each on the order of 20 to 100 um in diameter. The fibers 12 decollimate the collimated output beam by terminating in a plastic decollimating matrix 14 which supports and directs the fibers to deliver the UV radiation, simultaneously and at angles to all portions of the cornea, angling of each subdivided beam emerging from the optical fiber is always away from the optical axis of the eye, so that no radiation can reach the retina 2 shown in FIG. 2. Further, the small amount of radiation entering the cornea 5, of the eye is directed to the peripheral regions of the eye, thereby avoiding exposure to the lens 3 and the iris. Next, the matrix 14 may be contoured to fit over a quartz contact lens, the corneal-side curvature of which is predetermined for the particular patient. Such a lens may be used to accommodate particular requirements or preferences. A liquid interface will be constrained between the contact lens and the corneal surface 5. When a lens is not used, the liquid will be constrained between the cornea and the confronting surface of the decollimating matrix. The properties of the liquid interface are inertness with respect to corneal tissue; resistance to ablation from the UV radiation; and a UV absorbance (thermal conversion) proportional to the depth of the fluid.

Because of the existing limitation of attenuation of far UV radiation in quartz fibers (namely, some 30% per mm in the 200 nm region), the length of the fiber optic assembly 12 is preferably restricted to about 1 to 2 mm. As such, the combination of fiber-optic bundle, decollimating matrix, and contact lens resembles a single thick contact lens, as shown in FIG. 3. Here the laser output is moved closer to the eye, and to avoid inadvertent exposure of non-targeted eye/skin areas, baffling 15 is provided.

When corneal ablation to correct myopia is undertaken, the matrix 14 and contact lens when used in proximity with the cornea, is shallower than the surface of the cornea. The film thickness of the UV absorbing fluid is shallower at the center of the cornea than at its periphery, the greatest rate of ablation occurs at the center, gradually diminishing towards the periphery. The overall effect is to ablate the cornea so the its shape automatically approaches that of the contact lens surface, thereby correcting the illustrated myopic (nearsighted) condition.

The angled array of fibers in the decollimating matrix region is shown as one possible orientation of the fiber strands near the optical axis of the eye, this central region of the cornea can be uniformly irradiated while directing the beams of radiation from each of the fibers away from the central axis (on which the retina of the eye lies).

I claim:

1. A method to ablate the full surface of the cornea to achieve refractive correction, comprising the steps of:
   providing a liquid which is photo-dissociated by ultraviolet radiation no more than the compound glycerin;
   applying said liquid to the surface of the cornea;
   placing a far ultraviolet transparent contact lens having a concave side over said liquid such that the liquid completely fills the space between the outer surface of the cornea and the concave side of the contact lens;
   directing a collimated beam of far ultraviolet radiation into one end of a bundle of optic fibers, said fibers being aligned with said beam with each fiber intercepting substantially equal amounts of said radiation;
   selectively angling said fibers at another end of said bundle by a decollimating matrix to produce a constrained radiation directed towards of the surface of the cornea;
   passing said constrained radiation through said contact lens;
   attenuating said constrained radiation proportional to the thickness of said liquid thereby controlling the radiation reaching the cornea to cause the surface of the cornea to gradually be ablated to match the concave surface of said contact lens.

2. A method according to claim 1 wherein the step of selectively angling said fibers includes the step of angling so as to minimize the amount of ultraviolet radiation reaching portions of the eye other than the cornea.

3. A method according to claim 1 wherein the step of attenuating said radiation includes the step of attenuating the radiation without said radiation causing excessive heat buildup in said liquid; without said radiation significantly ablating said liquid; without said radiation causing a chemical change in said liquid.

4. A method according to claim 1 wherein the step of providing said liquid includes the step of providing a liquid which is both inert and partially transparent to said radiation; said liquid being the organic compound glycerin.

5. A method comprising performing the steps of claim 1 iteratively, wherein in the step of providing said liquid includes removing the old liquid to remove ablation products therein contained and providing fresh liquid.

6. A method according to claim 1 wherein the step of providing liquid includes providing a continuous laminar flow of said liquid between said contact lens and the surface of the cornea.

* * * * *